(12) United States Patent
Javitt et al.

(10) Patent No.: US 9,064,034 B2
(45) Date of Patent: Jun. 23, 2015

(54) HANDHELD BLOOD GLUCOSE MONITORING DEVICE WITH MESSAGING CAPABILITY

(71) Applicant: Telcare, Inc., Bethesda, MD (US)

(72) Inventors: Jonathan C. Javitt, Chevy Chase, MD (US); John R. Dwyer, Potomac, MD (US); Thomas Y. S. Shen, Hsinchu (TW); Benjamin Cheng Yu Shen, Hsinchu (TW); Ching-Yuan Chu, Hsinchu (TW)

(73) Assignees: Telcare, Inc., Bethesda, MD (US); Apex Biotechnology Corporation, Hsinchu (TW)

( * ) Notice: Subject to any disclaimer, the term of this patent is extended or adjusted under 35 U.S.C. 154(b) by 0 days.

(21) Appl. No.: 13/621,656

(22) Filed: Sep. 17, 2012

(65) Prior Publication Data

US 2013/0112557 A1 May 9, 2013

Related U.S. Application Data

(63) Continuation of application No. 13/364,130, filed on Feb. 1, 2012, now abandoned, which is a continuation-in-part of application No. 13/293,046, filed on Nov. 9, 2011.

(51) Int. Cl.
*G06F 19/00* (2011.01)
*G01N 27/327* (2006.01)
(Continued)

(52) U.S. Cl.
CPC .......... *G06F 19/322* (2013.01); *A61B 5/14532* (2013.01); *G06F 19/3418* (2013.01);
(Continued)

(58) Field of Classification Search
CPC ..... G01N 27/48; G01N 27/26; G01N 27/327; G06F 19/322; G06F 19/3418; G06F 19/345; A61B 5/0022; A61B 5/7435
USPC ............ 204/403.01–403.15; 422/68.1, 82.01; 435/287.1; 600/345
See application file for complete search history.

(56) References Cited

U.S. PATENT DOCUMENTS 6,295,506 B1 * 9/2001 Heinonen et al. ............. 702/104
7,188,484 B2 * 3/2007 Kim ............................. 62/259.2
(Continued)

FOREIGN PATENT DOCUMENTS

WO   WO 2006/092323 A1   9/2006
WO   WO 2009/005950    *  1/2009
(Continued)

OTHER PUBLICATIONS

International Search Report directed to related International Patent Application No. PCT/US2012/063961, mailed Oct. 8, 2013; 6 pages.
(Continued)

*Primary Examiner* — Jennifer Dieterle
(74) *Attorney, Agent, or Firm* — Sterne, Kessler, Goldstein & Fox P.L.L.C.

(57) ABSTRACT

A patient monitoring network pertaining to blood glucose and other analyte measurements includes wireless blood glucose or other analyte measuring devices and a networked computer or server. Each monitoring device is associated with a patient and is configured to measure the glucose level or other analyte from a given blood sample via inserted test strips, transmit the measurements to the networked computer, and display received messages. The blood glucose monitoring device includes means for substantially reducing factors that could affect the glucose measurement such as thermal and RF interference.

8 Claims, 13 Drawing Sheets

(51) Int. Cl.
  *A61B 5/145* (2006.01)
  *G01N 33/487* (2006.01)
  *A61B 5/00* (2006.01)
  *A61B 5/15* (2006.01)

(52) U.S. Cl.
  CPC ............ *G06F19/345* (2013.01); *A61B 5/7435* (2013.01); *A61B 5/0022* (2013.01); *G01N 27/3274* (2013.01); *G01N 33/48792* (2013.01); *A61B 2560/0252* (2013.01); *A61B 2560/0266* (2013.01); *A61B 2562/182* (2013.01); *G01N 27/3273* (2013.01); *A61B 5/7465* (2013.01); *A61B 5/150854* (2013.01)

(56) References Cited

U.S. PATENT DOCUMENTS

| | | | |
|---|---|---|---|
| 8,073,503 | B2 † | 12/2011 | Hoefel |
| 2004/0214345 | A1 † | 10/2004 | Matzinger |
| 2005/0019848 | A1 | 1/2005 | Lee et al. |
| 2005/0038680 | A1 | 2/2005 | McMahon |
| 2006/0229502 | A1* | 10/2006 | Pollock et al. ............... 600/300 |
| 2008/0294024 | A1* | 11/2008 | Cosentino et al. ........... 600/309 |
| 2009/0210190 | A1* | 8/2009 | Carlson et al. ............... 702/130 |
| 2009/0325205 | A1 | 12/2009 | Fujii et al. |
| 2010/0026995 | A1* | 2/2010 | Merritt et al. ................ 356/222 |
| 2010/0069730 | A1 | 3/2010 | Bergstrom et al. |
| 2010/0128754 | A1 | 5/2010 | Jetter et al. |
| 2010/0268052 | A1* | 10/2010 | Asama et al. ................. 600/365 |
| 2010/0307916 | A1 | 12/2010 | Ramey et al. |
| 2011/0063094 | A1 | 3/2011 | Meiertoberens et al. |
| 2011/0237916 | A1 | 9/2011 | Hanson et al. |
| 2012/0095311 | A1* | 4/2012 | Ramey et al. ................ 600/365 |
| 2012/0095312 | A1 † | 4/2012 | Ramey |
| 2012/0253150 | A1 † | 10/2012 | Merritt |

FOREIGN PATENT DOCUMENTS

| | | |
|---|---|---|
| WO | WO 2011/081211 A1 | 7/2011 |
| WO | WO 2012/049238 A1 | 4/2012 |

OTHER PUBLICATIONS

Written Opinion of the International Searching Authority directed to related International Patent Application No. PCT/US2012/063961, mailed Oct. 8, 2013; 12 pages.

English-Language Abstract for International Patent Application Publication No. WO 2006/092323 A1, published Sep. 8, 2006; 1 page.

English-Language Abstract for International Patent Application Publication No. WO 2011/081211 A1, published Jul. 7, 2011; 1 page.

International Preliminary Report on Patentability drected to related International Patent Application No. PCT/US2012/063961, mailed May 22, 2014.

\* cited by examiner
† cited by third party

600

502 ← Patient Name  (Active since Date) 504
Diabetes Type 2

| METER SERIAL NUMBER | ACTIVATION DATE (MM/DD/YYYY) | PRESCRIBED READINGS | TYPE OF DIABETES |
|---|---|---|---|
| | | | |

610 — Before Meal    NORMAL RANGE: [606] TO: [ ]    HIGH MAX: [608]

612 LOW: 20 - 85   NORMAL: 85 - 135   HIGH: 135 - 275   VERY HIGH: >275
     613a    613b                     613c

After Meal    NORMAL RANGE: [ ] TO: [ ]    HIGH MAX: [ ]

LOW: 20 - 90   NORMAL: 90 - 165   HIGH: 165 - 255   VERY HIGH: >255

Before Exercise    NORMAL RANGE: [ ] TO: [ ]    HIGH MAX: [ ]

LOW: 20 - 75   NORMAL: 75 - 185   HIGH: 185 - 265   VERY HIGH: >265

After Exercise    NORMAL RANGE: [ ] TO: [ ]    HIGH MAX: [ ]

LOW: 20 - 85   NORMAL: 85 - 160   HIGH: 160 - 275   VERY HIGH: >275

Night    NORMAL RANGE: [ ] TO: [ ]    HIGH MAX: [ ]

LOW: 20 - 70   NORMAL: 70 - 150   HIGH: 150 - 280   VERY HIGH: >280

HANDHELD BLOOD GLUCOSE MONITORING DEVICE WITH MESSAGING CAPABILITY

CROSS REFERENCE TO RELATED APPLICATIONS

This application is a continuation of U.S. patent application Ser. No. 13/364,130, filed Feb. 1, 2012, which is a continuation-in-part of U.S. patent application Ser. No. 13/293,046, filed Nov. 9, 2011, each of which is incorporated herein by reference in its entirety.

BACKGROUND

1. Field of the Invention

The invention relates to wireless medical devices for collecting information from patients at remote locations and, more particularly, to handheld glucose monitoring devices for wirelessly communicating blood glucose and other analyte readings from patients to a remote server and for communicating related information from the server back to the patients.

2. Background

Diabetes is a metabolic disease in which a person has high blood sugar either due to the body's inability to produce insulin, or the cells inability to respond to insulin. The disease can cause numerous complications, both short-term and long-term, and ultimately death if not well treated. Diabetes is the seventh leading cause of death in the United States by disease with nearly 284,000 deaths reported in 2007.

Medical expenditures on those living with diabetes in the United States have steadily increased every year. People with diabetes have medical costs that are nearly 2.5 times higher than those without the disease. From 1980 through 2007, the number of Americans with diabetes quadrupled from 5.6 million to 23.6 million, accounting for 8% of the total U.S. population. Based on these numbers, the U.S. has spent over 174 billion dollars on caring for those diagnosed with diabetes in 2007 alone, a figure that makes up nearly 40% of the worldwide cost for treating diabetes. U.S. spending on diabetes is expected to rise to over 336 billion dollars by the year 2034.

One of the factors leading to high costs for diabetes treatment is the issue of patient non-compliance. It is vital that patients diagnosed with diabetes regularly measure their blood glucose levels throughout the day and self-administer insulin injections if necessary. Failure to do so can lead to more hospitalizations and potentially create further health problems, all of which increase medical costs. On average, the annual medical costs per patient are nearly 3000 dollars higher for non-compliant patients versus those who regularly track their blood glucose levels. It is therefore an important initiative to improve the level of patient compliance as it pertains to effective treatment for diabetes.

Current treatment protocols and methods rely entirely on the self-motivation of the patient to measure and record the results of their blood glucose levels which requires a high level of individual attention.

What is needed is a treatment protocol that improves patient compliance and improves treatment by facilitating real-time communication to and from the patient.

SUMMARY

In an embodiment, a handheld blood glucose monitoring device is described. The device includes a glucose sensing subsystem, a radio transceiver subsystem, and a display. The glucose sensing subsystem is configured to measure a blood glucose level in a blood sample. The radio transceiver subsystem is configured to receive blood glucose measurements from the glucose sensing subsystem, to transmit the blood glucose measurements over a wireless communications link, and to receive over the wireless communications link a message returned to the handheld device in response to the transmitted blood glucose measurement. The display is configured to display blood glucose measurements from the glucose sensing subsystem and to display the message received from the radio transceiver subsystem. The device further includes means for substantially reducing RF interference caused by the radio transceiver subsystem, and means for mitigating the effects of heat generated by the device on a temperature sensor coupled to the device, In an alternate embodiment, the handheld monitoring device can be used to monitor other analytes. For, example, the blood glucose sensor may be replaced with a sensor to monitor interstitial fluid glucose, blood coagulation factors, cardiac enzymes, catecholamines, and other biomarkers. Such alternate sensors may operate, for example, using electrochemical or colorimetric sensing techniques as would be apparent to a person skilled in the relevant art.

In this alternate embodiment, similar to the blood glucose monitoring device, the handheld analyte monitoring device includes an analyte sensing subsystem configured to measure an analyte from a patient, and a radio transceiver subsystem configured to receive analyte measurements from the analyte sensing subsystem and to transmit the analyte measurements over a wireless communications link. Similar to the blood glucose monitoring system, the handheld analyte monitoring device further includes means for substantially reducing RF interference caused by the radio transceiver subsystem, and means for mitigating the effects of heat generated by the device on a temperature sensor coupled to the device.

Another embodiment of the invention includes a test strip for receiving a liquid sample, which may be used in either the glucose monitoring device or the analyte monitoring device. The test strip includes a reservoir channel for receiving the liquid sample, one or more measurement electrodes disposed within the reservoir channel, one or more contact electrodes, and a temperature sensor disposed substantially at or near the one or more measurement electrodes. The test strip further includes means for electrically coupling the measurement electrodes to the contact electrodes.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

FIG. 6 illustrates a screenshot of a clinical profile, according to an embodiment.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications beyond diabetes care.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

Figure 1:
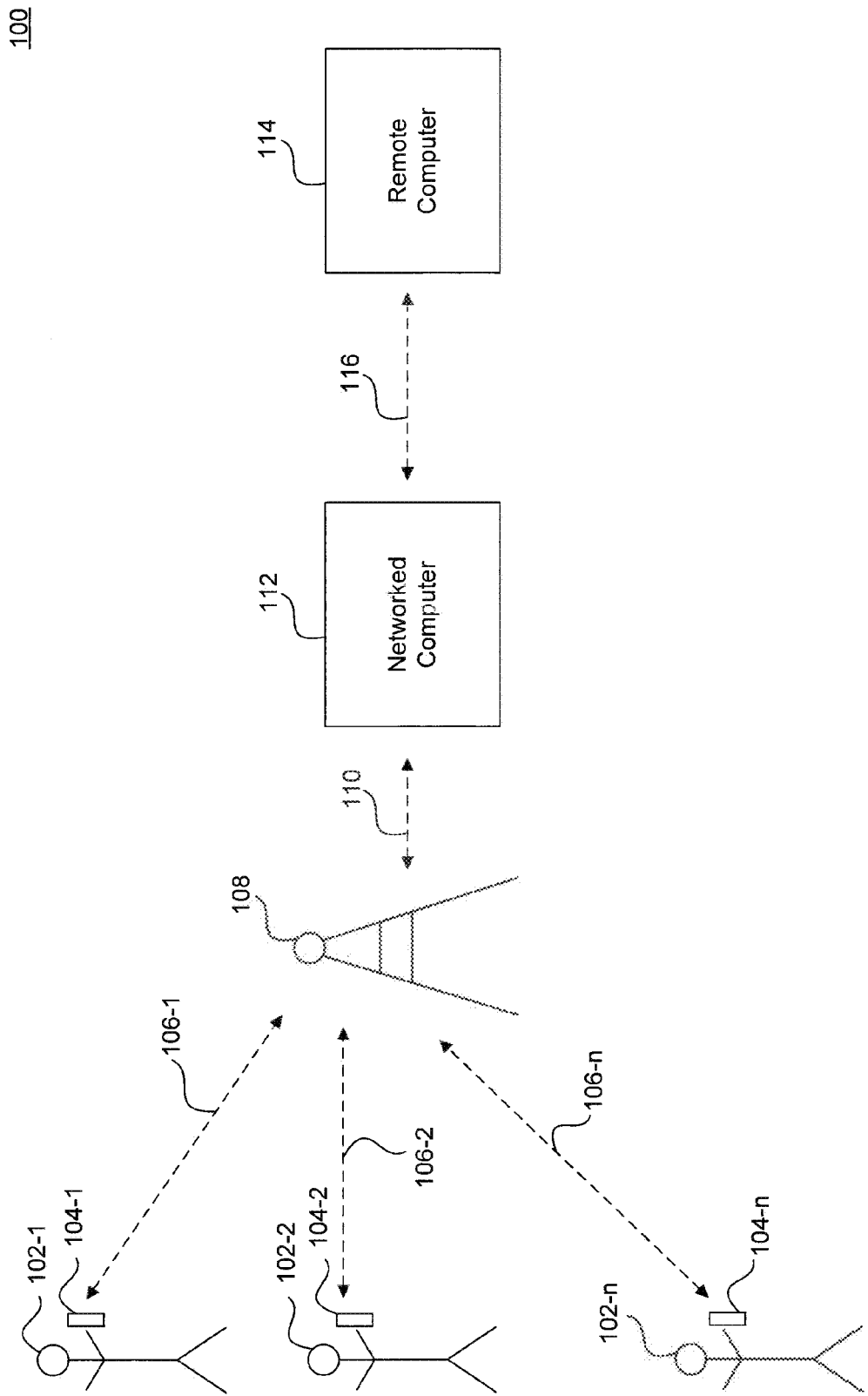
FIG. 1 illustrates a patient monitoring network, according to an embodiment.

FIG. 1 illustrates an exemplary patient monitoring system or network 100 according to an embodiment. Patient monitoring network 100 includes a plurality of n blood glucose monitoring devices 104-1 to 104-n, each associated with a respective patient 102-1 to 102-n. Patient monitoring network 100 further includes a networked computer 112 and a remote computer 114. In an embodiment, each blood glucose monitoring device 104-1 to 104-n communicates wirelessly to a cellular telephone tower 108 ("cell tower 108") via a respective wireless communications link 106-1 to 106-n. In an embodiment, cell tower 108 communicates with networked computer 112 via communications link 110, and remote computer 114 communicates with networked computer 112 via communications link 116. Communication links 110 and 116 can include any network or combination of networks including, for example, the global Internet, a wide area network (WAN), metropolitan area network (MAN), wireless network, telephone network, or local area network (LAN).

Networked computer 112 may include, for example, one or more standalone computers, a server, a virtual server, a server farm, of a cloud-computing server. In an embodiment, wireless communications link 106 may use any transmission means, or combination thereof, known to a person skilled in the art which include, for example, WiFi, Bluetooth, satellite, 2G cellular, 3G cellular, 4G cellular, etc. In one preferred embodiment, communications link 106 includes 3G cellular communications.

A patient using a blood glucose monitoring device 104 within patient monitoring network 100 may use device 104 to take a reading (i.e., a measurement) of their blood glucose level from a blood sample. The measurement can be transmitted to networked computer 112, where the measurement is stored in a record of a database. Each stored record is associated with a particular patient.

In an embodiment, the blood glucose monitoring device 104 can also receive one or more messages transmitted from the networked computer 112. In an embodiment, blood glucose monitoring device 104 receives a message as a result of transmitting a glucose reading to networked computer 112. The received one or more messages may contain information relating to the most recent blood glucose measurement, information relating to past blood glucose measurements, and/or one or more personalized messages for the particular patient associated with the blood glucose monitoring device. In another example, networked computer 112 tracks the number of glucose test strips used by the patient (based on, for example, the number of blood-glucose measurements uploaded from device 104 to networked computer 112) and, when the number of test strips remaining is low (e.g., determined, for example, by comparing the number of measurements to a threshold value), transmits a low-supply message to blood glucose monitoring device 104, thereby alerting the patient to order more test strips. In addition, the patient may use blood glucose monitoring device 104 to transmit a response to the one or more messages back to networked computer 112. The response may include, for example, an order for more test strips. Test strip usage tracking and replacement strip ordering is discussed in more detail below.

One or more of the records (e.g., an authorized subset of records) stored on the database of networked computer 112 may be accessed via remote computer 114. Remote computer 114 may be any device capable of accessing and displaying the records stored on the database of networked computer 112 including, but not limited to, a smartphone, a computer (e.g., a personal computer or PC), a tablet PC, etc. In an embodiment, a patient may use remote computer 112 to access their own record. The record may contain summaries of all of the patient's past blood glucose readings in various graphical formats and can allow customization by the patient as is explained in more detail below. In an embodiment, a caregiver may use remote computer 112 to access the records of all the patients under supervision of the caregiver. The caregiver may have access to graphical summaries and data lists of blood glucose readings for all of their patients. In an embodiment, the caregiver accesses a script editor to allow for customization of messages to be transmitted to each blood glucose monitoring device 104 and when each message is to be transmitted. The utility of the script editor is explained in more detail below.

Figure 2:
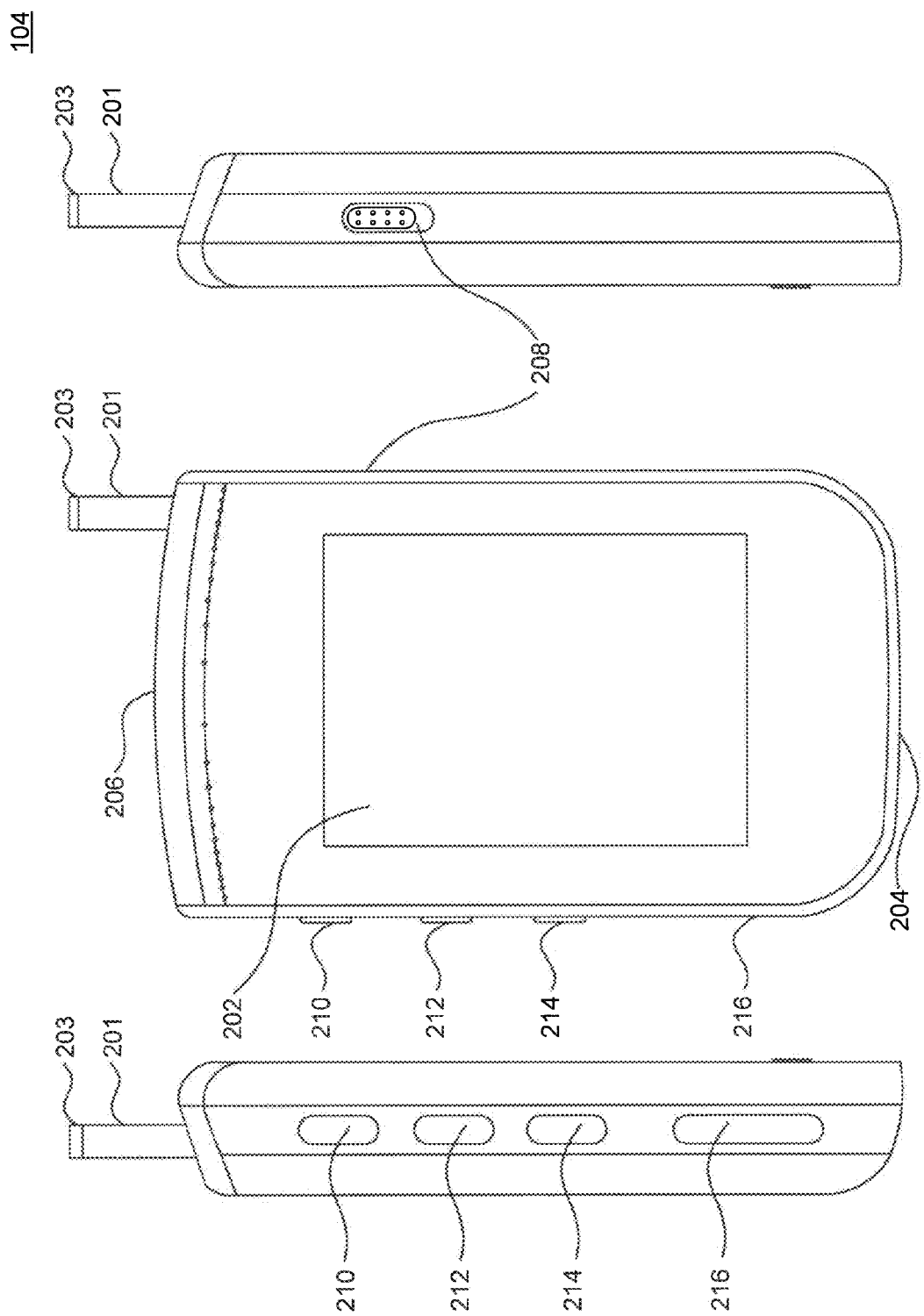
FIG. 2 illustrates an embodiment of a blood glucose monitoring device.

FIG. 2 depicts left-side, front-side and right-side views of an embodiment of a blood glucose monitoring device 104. Blood glucose monitoring device 104 includes a display 202, a connection port 204, a test strip port 206, a power button 208, and a SIM card door 216. In an embodiment, blood glucose monitoring device 104 also includes a user interface (e.g., to receive user input) which comprises buttons along the side of blood glucose monitoring device 104. The buttons may include an up button 210, an enter (or select) button 212 and a down button 214. In another embodiment, display 202 may be a touch-screen display (i.e., a touch-sensitive display) to act as the user interface in lieu of or in addition to buttons 210-214.

Display 202 may utilize any technology known to those skilled in the art, including, but not limited to, LCD, OLED, TFT LCD, etc. In an embodiment, display 202 is configured to show the most recent blood glucose reading taken by blood glucose monitoring device 104. Display 202 may also show a graphical indication of a comparison between the most recent blood glucose reading taken and a target blood glucose level. In an embodiment, display 202 shows any messages received from networked computer 112.

Test strip port 206 allows for the insertion of a blood glucose test strip. Blood glucose test strips are disposable strips used to collect a small blood sample from a patient as is known by those skilled in the art. The test strip may contain chemicals which react with the glucose preset in the blood and produce a calibrated current response curve to an applied voltage. The calibration curve is generated by calibrating each manufactured test strip lot against known blood standards using a laboratory reference instrument, such as a Yellow Springs Instrument (YSI) glucose analyzer. This calibration curve is converted to a calibration code that is imprinted on the glucose test strip using conductive ink in order to enable blood glucose monitoring device 104 to identify the correct calibration curve to apply to the signal generated by the test strip, according to an embodiment. A total of seven (7) calibration curves are stored inside the firmware of blood glucose monitoring device 104, according to an embodiment. In one example, identification of code and selection of calibration curve is performed automatically upon placing the test strip into test strip port 206, and no code number is displayed to the patient. Power button 208 may be any suitable switch to turn the power on and off to the device including, but not limited to, a slider, a toggle switch, a push button, etc. It should be understood that although power button 208 is illustrated in FIG. 2 to be located on the side of blood glucose monitoring device 104, power button 208 may be located anywhere on blood glucose monitoring device 104.

SIM card door 216 may be used to protect a subscriber identity module (SIM) card placed therein. The use of SIM cards is well known to a person skilled in the art. In an embodiment, the SIM card within blood glucose monitoring device 104 allows unique identification of blood glucose monitoring device 104 within patient monitoring network 100.

Each button associated with the user interface of blood glucose monitoring device 104 allows the patient to provide input. For example, up button 210 and down button 214 may be used to scroll through menu options displayed on display 202, while enter button 212 allows for the selection of a particular menu option. In another example, up button 210 and down button 214 may be used to scroll through answer options for a message received from networked computer 112 and displayed on display 202, while enter button 212 may be used to choose an answer option and execute the transmission of the chosen answer option to networked computer 112. In another example, the user interface may be utilized by the patient to facilitate the ordering of more test strips upon receiving a message alerting the patient to order more. It should be understood that although up button 210, enter button 212, and down button 214 are illustrated in FIG. 2 to be located on the side of blood glucose monitoring device 104, each button may be located anywhere on blood glucose monitoring device 104. Further, these three buttons may be implemented as features of a touch-sensitive display.

The calibrated current response, produced from the reaction of glucose within a blood sample with the chemicals on the test strip, may be sensitive to ambient environmental conditions. For example, the chemicals on the test strip may contain enzymes which react with the glucose in a blood sample. These enzymes have a reaction rate which is dependent upon the temperature. Thus, successful calibration may also require knowledge of the temperature during the reaction. For this reason, a temperature sensor may be utilized in conjunction with the blood glucose measurements.

However, there are challenges with the incorporation of a temperature sensor in the embodied blood glucose monitoring device. Components of the blood glucose monitoring device, such as batteries, active circuit components, and the display, will generate heat that can raise the temperature readings of any temperature sensor placed in the same enclosure. The test strip, however, may not be affected by the same heat, since the test strip will typically be located right at the interface between the monitoring device's housing and the exterior environment (i.e., ambient temperature). This may result in the temperature sensor indicating a temperature that is different from what the reaction on the test strip (i.e., at the electrochemical reaction site) is actually experiencing.

One solution to this challenge is to locate the temperature sensor remotely from the device's various sources of thermal energy. For example, the temperature sensor may be disposed within the housing of the device 104 but may be thermally segregated from the components primarily responsible for generating the heat that causes the thermal interference. This may be accomplished by subdividing the housing into different compartments and by providing ventilation openings in the outer walls to allow convection cooling of each compartment. In an embodiment shown in FIG. 2, a stalk 201 may be added to blood glucose monitoring device 104 to provide an external probe away from the main body of the device. A temperature sensor 203 may be disposed at the end of stalk 201, allowing for measurement of the ambient air temperature while minimizing thermal interference from the components of blood glucose monitoring device 104.

Figure 13:
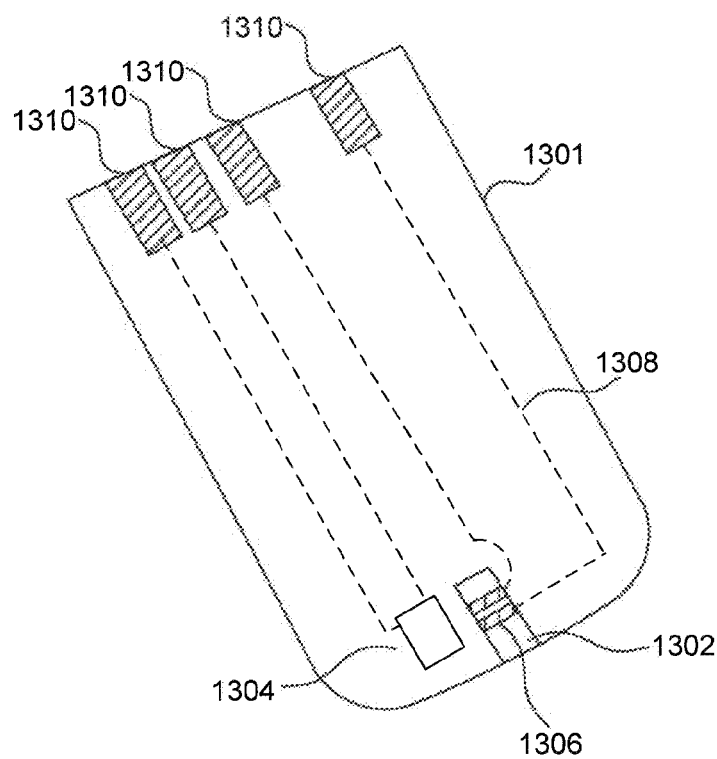
FIG. 13 is an illustration of a test strip, according to an embodiment.

In another embodiment, the temperature sensor may be disposed directly on the test strip. FIG. 13 illustrates a test strip 1300 for use in a monitoring device such as, for example, blood glucose monitoring device 104. Test strip 1300 includes a temperature sensor 1304 disposed on a body portion 1301 (e.g., a plastic substrate such as is commonly used for test strips), according to an embodiment. Test strip 1300 may further include a reservoir channel 1302, measurement electrodes 1306, electrical leads 1308, and contact electrodes 1310, each disposed on body portion 1301. A liquid sample, for example, blood, is placed on reservoir channel 1302 where it comes into contact with measurement electrodes 1306. Then, when a voltage is applied across measurement electrodes 1306 by, for example, blood glucose monitoring device 104, an electrochemical reaction is produced at the measurement electrodes, generating a current based on the concentration of an analyte, for example, glucose, within the liquid sample. The current is measured via contact electrodes 1310 by a monitoring device such as, for example, blood glucose monitoring device 104.

Temperature sensor 1304 may be placed substantially near to measurement electrodes 1306, providing an accurate temperature reading at the site of the electrochemical reaction. Temperature sensor 1304 may be any sensor known to those skilled in the art including, but not limited to, a thermocouple, a resistive sensor, etc. The resistive sensor may include, for example, a metallic material with a resistance that varies with temperature, or a semiconductor material with a resistance that varies with temperature. It should be understood that temperature sensor 1304 may also be disposed at any location on test strip 1300.

The various electrodes illustrated in FIG. 13 are only an example of possible electrode arrangement on test strip 1300 and are not meant to be limiting. Contact electrodes 1310 may provide electrical coupling to both measurement electrodes 1306 and temperature sensor 1304. Additionally, contact electrodes 1310 and measurement electrodes 1306 are electrically coupled via conductive leads 1308, according to an embodiment. Conductive leads 1308 may be hidden from the view of a user by disposing them within plastic body 1301, according to an embodiment. Conductive leads 1308 may also be used to provide electrical coupling between contact electrodes 1310 and temperature sensor 1304.

Figure 3:
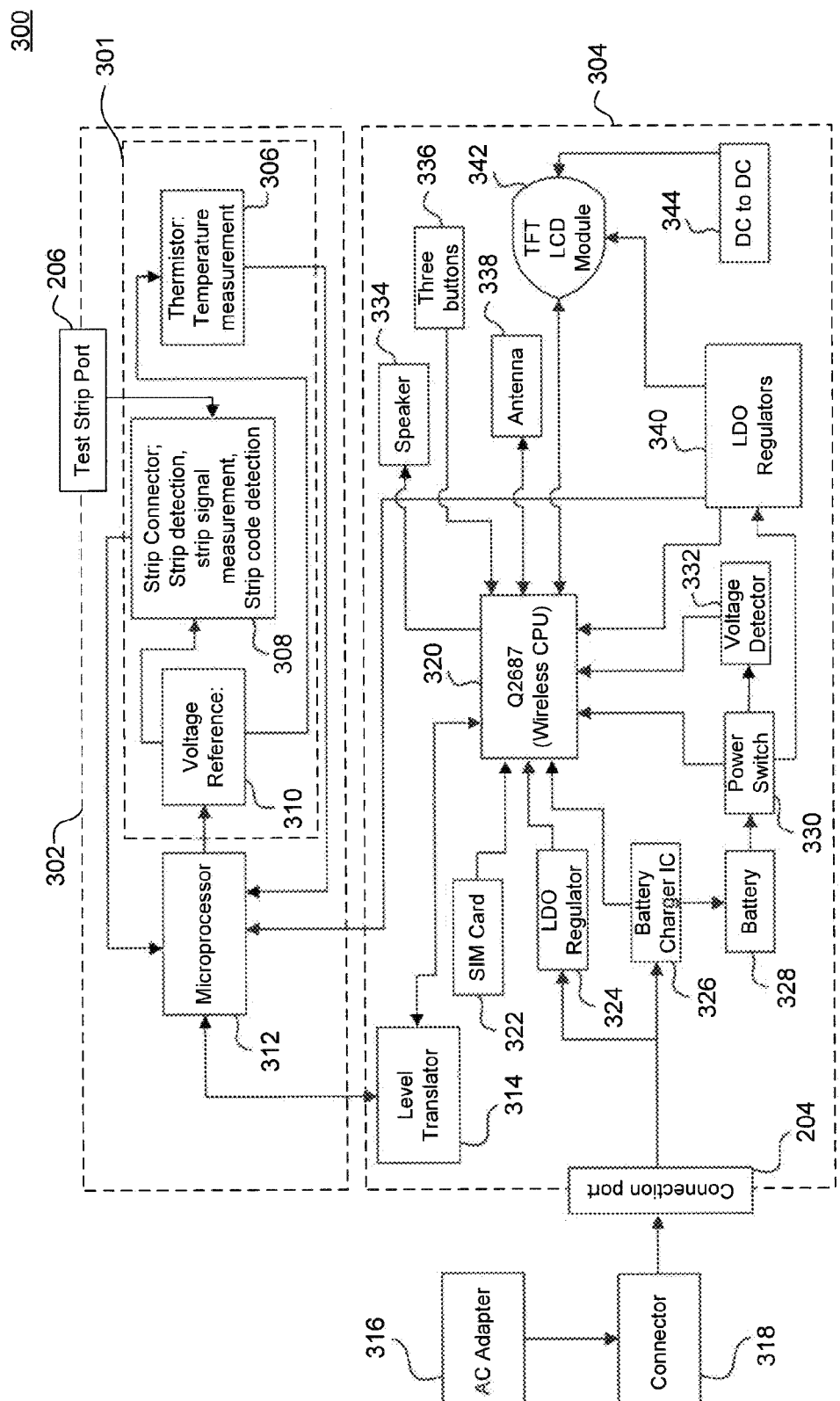
FIG. 3 illustrates a subsystem diagram of a blood glucose monitoring device, according to an embodiment.

FIG. 3 illustrates a subsystem-level block diagram 300 of blood glucose monitoring device 104. Subsystem diagram 300 includes, at a high level, a glucose sensing subsystem 302 and a radio transceiver subsystem 304. In an embodiment, the components of glucose sensing subsystem 302 are configured to measure a blood glucose level from a blood sample on a test strip placed into test strip port 206. In an embodiment, the components of radio transceiver subsystem 304 are configured to receive blood glucose measurements from glucose sensing subsystem 302, and transmit the blood glucose measurements to networked computer 112 over a wireless communications link. In an embodiment, radio transceiver subsystem 304 is further configured to receive over the wireless communications link a message in response to the transmitted blood glucose measurement. Radio transceiver subsystem 304 may include a cellular radio, either CDMA or GSM, using GPRS data transmission protocols for communicating over the wireless communications link.

In an embodiment, a temperature sensor 306 is included within glucose sensing subsystem 302. In one embodiment, temperature sensor 306 is implemented within the same housing or enclosure with glucose sensing subsystem 302. In another embodiment, temperature sensor 306 is implemented as temperature sensor 203 disposed at the end of stalk 201. In yet another embodiment, temperature sensor 306 is implemented as temperature sensor 1304 on test strip 1300.

In an embodiment, a strip detector unit 308 is also included to determine the type of test strip inserted and to measure the current response from the test strip. In one example, strip detector unit 308 includes calibration data for seven (7) different test strip codes. In an embodiment, a voltage reference 310 is applied to the test strip electrodes during the measurement. In one example, voltage reference 310 has a value of 415 mV. A microprocessor 312 controls operation of glucose sensing subsystem 302.

A microcontroller 320 within radio transceiver subsystem 304 controls radio transceiver subsystem 304. In one preferred embodiment, microcontroller 320 controls all of the components within both radio transceiver subsystem 304 and glucose sensing subsystem 302. In an embodiment, level translator 414 is included to translate the voltage level between microprocessor 312 and microcontroller 320. In an embodiment, microcontroller 320 interfaces with numerous components such as a SIM card 322, a speaker 334, an antenna 338, a user interface 336, and a display module 342. In an embodiment, a power switch 330 is used to control power provided from a battery 328 to the components of device 104 including a voltage detector 332 and a voltage regulator bank 340. Voltage regulator bank 340 may comprise one or more low drop out (LDO) voltage regulators, the use of which is well known to those skilled in the art. Voltage regulator bank 340 provides stable low voltage levels to microcontroller 320, microprocessor 312 and display module 342. Voltage regulator bank 340 also provides stable low voltage levels to display module 342 via a DC to DC converter 344. In an example, voltage regulator bank 340 provides voltage outputs of 3 V, 2.8 V or 1.8 V.

In an embodiment, microcontroller 320 can control the operation of various components within transceiver subsystem to mitigate the effects of heat produced by the components. For example, the heat generated from a battery charger 326 may be controlled to prevent a rise in the temperature above a certain threshold. In an example embodiment, the temperature substantially near battery 328 may be controlled to not rise more than two degrees Fahrenheit above ambient conditions. Controlling the operation of battery charger 326 may involve, for example, the use of pulse-width modulation or changing the charging voltage. Alternatively, the thermal output substantially near microcontroller 320 may be controlled to prevent a rise in the temperature above a certain threshold. In an example embodiment, the temperature substantially near microcontroller 320 may be controlled to not rise more than two degrees Fahrenheit above ambient conditions. Controlling this temperature may involve active cooling systems or changing the clock speed of microcontroller 320.

Antenna 338 may be any antenna suitable for use within a standard mobile communications device such as a 2G cellular telephone. Examples of antennas include, but are not limited to, patch antennas, strip antennas, ceramic antennas, dipole antennas, whip antennas, etc.

The RF radiation generated from antenna 338 may interfere with the electrochemical measurements performed by glucose sensing subsystem 302. In an embodiment, glucose sensing subsystem 302 and radio transceiver subsystem 304 are substantially isolated within blood glucose monitoring device 104 in order to minimize the RF interference between the two subsystems. The isolation may be realized by providing each subsystem on its own separate printed circuit board (PCB).

In another embodiment, RF interference may be further reduced by disposing a shielding structure 301 around at least a portion of glucose sensing subsystem 302. In an example, shielding structure 301 surrounds temperature sensor 306, strip connector 308 and voltage reference 310. Shielding structure may alternatively be disposed around all the components of glucose sensing subsystem 302. Shielding structure 301 may be a Faraday cage which substantially attenuates external RF signals. The Faraday cage may be formed, for example, using a metallic foil.

In yet another embodiment, microcontroller 320 may deactivate RF emission from antenna 338 during a measurement time period when the electrochemical reaction is taking place on the test strip. Once glucose sensing subsystem 302 has successfully performed the measurement from the sample, microcontroller 320 may reactivate the RF transmission circuitry coupled to antenna 338.

Components which exist external to the blood glucose monitoring device include an AC adapter 316 for providing useable current from a common electrical outlet, and a connector 318 for connecting AC adapter 316 to connection port 204 of device 104. Connector 318 may be any suitable connector that can exist between two electronic or electrical sources including, but not limited to, USB, micro USB, IEEE 1394 (Firewire), etc. In an embodiment, connector 318 may be used to link connection port 204 to a computer. Connection port 204 is configured to allow current to flow to either a battery charger 326 or a voltage regulator 324.

Figure 4:
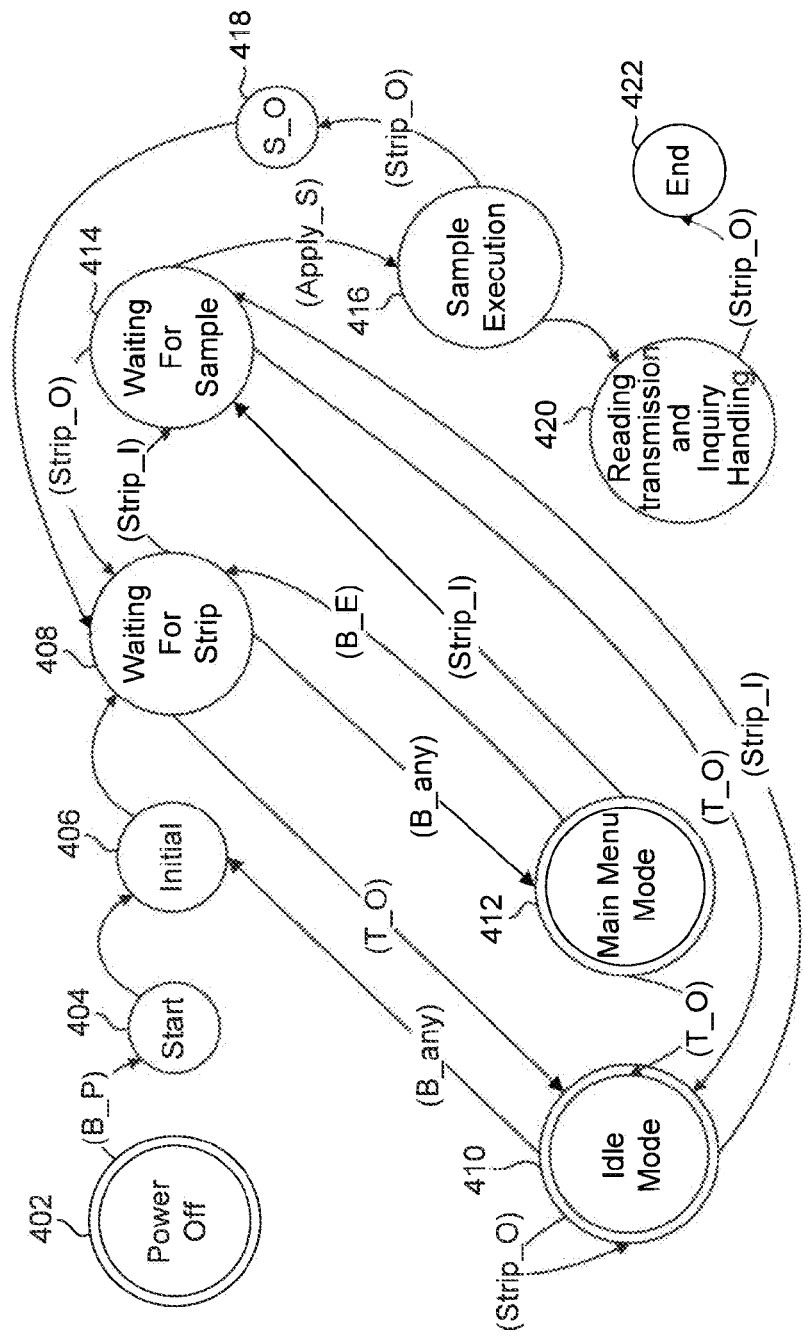
FIG. 4 illustrates a state transition diagram of a blood glucose monitoring device, according to an embodiment.

FIG. 4 illustrates a state transition diagram 400 illustrating an example mode of operation of blood glucose monitoring device 104 according to an embodiment. The blood glucose monitoring device begins in the power off state 402. Starting state 404 is transitioned to when the power button on the blood glucose monitoring device is pressed (B_P) and further transitions to an initial state 406. Initial state 406 transitions to a waiting for strip state 408 without any input from the patient.

At state 408, a message is shown on the display of blood glucose monitoring device 104, prompting the patient to insert a test strip into the test strip port. In an example, pressing any button (B_any) associated with the user interface of device 104 transitions from state 408 to a menu state 412. In another example, state 408 transitions to an idle state 410 if no action is taken within a threshold time period. The threshold time period is, for example, 30 seconds. Inserting a test strip (Strip_I) causes device 104 to transition from state 408 to sample state 414.

At state 412, menu options are shown on the display of the blood glucose monitoring device. State 412 transitions to state 410 if no action is taken within a threshold time period. As mentioned above, the threshold time period is, for example, 30 seconds. A patient may use the user interface on the blood glucose monitoring device to prompt the device to wait for a test strip (B_E) which causes a transition from state 412 to state 408. Inserting a test strip (Strip_I) will also transition device 104 from state 412 to sample state 414.

At state 410, device 104 enters an idle mode and shuts the power off to the display in order to conserve energy. Pressing any button (B_any) associated with the user interface transitions device 104 from state 410 to state 406. Inserting a test strip (Strip_I) causes device 104 to transition from state 410 to sample state 414.

At state 414, device 104 waits to receive a blood sample on the test strip which has been placed into the test strip port. Removing the test strip (Strip_O) before a sample has been placed on the test strip causes a transition from state 414 to state 408. State 414 transitions to state 410 if no action is taken within a threshold time period. Again, the threshold time period is, for example, 30 seconds. State 414 transitions to sample execution state 416 once a blood sample has been placed on the test strip (Apply_S).

At state 416, the blood glucose level is measured from the sample. If the test strip is removed prior to the completion of the sample analysis, then state 416 transitions to a strip error state 418. If the measurement of the blood glucose level from the sample is completed, state 416 transitions to transmission state 420.

At strip error state 418, a message is shown on the display of device 104 alerting the patient that a measurement error occurred. State 418 transitions to state 408 to wait for a test strip to be placed back into the test strip port.

At state 420, the glucose measurement is transmitted to a networked computer in order to be stored in a patient's record within a database. The glucose measurement is shown on the display of device 104. State 420 transitions to ending state 422 when the test strip is removed (Strip_O).

The state transitions of device 104, illustrated in the exemplary embodiment of FIG. 4, are controlled by a computer program (e.g., software and/or firmware) residing in microprocessor 312 or, alternatively, in a memory (not shown) associated with microprocessor 312.

Referring back to FIG. 1, blood-glucose measurements from a plurality of monitored patients are stored in a database in networked computer 112. The database can then be accessed by remote computer 114 for analysis of the blood-glucose measurements. For example, in connection with analysis and/or display of the blood-glucose measurements on remote computer 114, FIGS. 5-8 shows exemplary screenshots that may be shown on a display associated with remote computer 114. It should be understood that any text or graphics shown are examples of possible text or graphics. A person skilled in the art would be capable of altering presentation of the blood-glucose data to achieve the same goals described herein without departing from the spirit or scope of the present invention.

The exemplary screenshots displayed in FIGS. 5-8 are associated with a computer program executed by a processor within remote computer 114.

Figure 5:
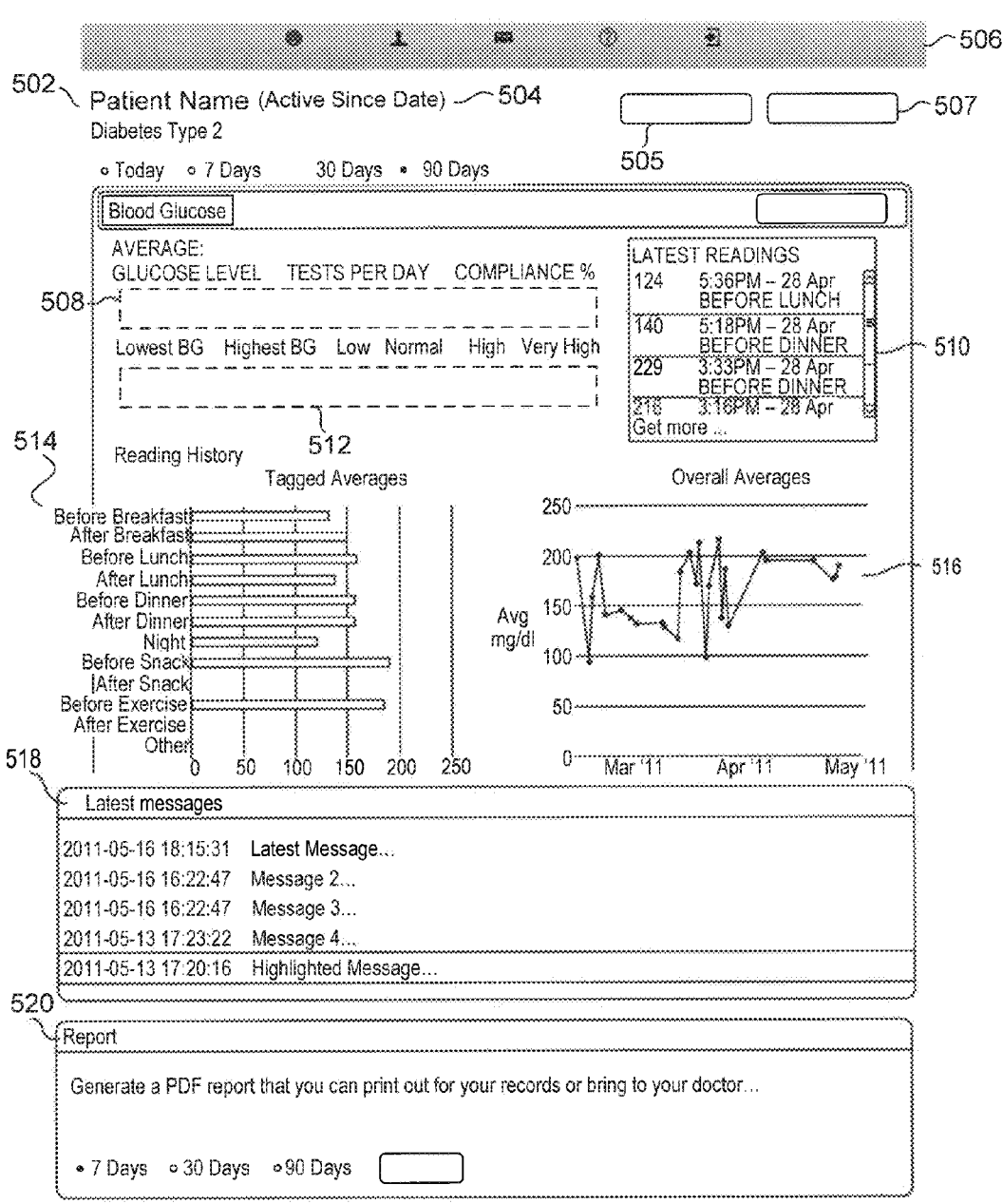
FIG. 5 illustrates a screenshot of a glucose data summary, according to an embodiment.

FIG. 5 illustrates a patient data summary screen 500 displaying glucose readings for a particular patient. The top portion of patient data summary screen 500 displays a patient name 502 associated with the record being shown, a date 504, a patient menu bar 506, a settings button 505 and an upgrade button 507. The middle portion of patient data summary screen 500 displays an average readings section 508, a latest readings table 510, a reading summary 512, a reading history 514, and an average readings graph 516. The bottom portion of patient data summary screen 500 displays a latest messages section 518 and a print report section 520.

Date 504 may be associated with the date that the patient activated their account within patient monitoring network 100. Alternatively, date 504 may be associated with the last time the record had been accessed by the patient. Any other dates of interest for the patient may be displayed as date 504.

Patient menu bar 506 may display icons allowing the user to navigate to other pages. For example, one icon returns the user to patient data summary screen 500 when selected. Another icon, when selected, may navigate a user to a friend's page allowing the user to select email addresses of others who would be allowed to view their record. Another icon, when selected, may navigate a user to a profile page, which allows the user to change basic profile information associated with the record such as the patient's name, patient's address, etc. Another icon, when selected, may navigate a user to a support page which allows the user to contact a technical support group for the software. Another icon, when selected, may allow the user to log out of the software program. Patient menu bar 506 may continue to exist at the top of the page regardless of the content shown on the rest of the page.

Settings button 505 may be selected to display a drop-down menu providing various menu options. For example, menu options such as messaging, clinical profile, or an HCP (health care provider) log may be displayed. The HCP log may include a list of all the dates and times that a licensed healthcare professional has accessed the current record.

In an embodiment, selecting the messaging menu option navigates the user to a page allowing the user to choose which default messages are sent to the blood glucose monitoring device associated with the record. In an embodiment, default messages are sent to the blood glucose monitoring device in response to a blood glucose measurement being transmitted by the device. Default messages may contain information relating the most recent blood glucose measurement to past measurements taken by the blood glucose monitoring device or information relating to a completion percentage of prescribed blood glucose measurements for the day.

In an embodiment, selecting the clinical profile menu option navigates the user to a patient clinical profile screen 600 exemplarily illustrated in FIG. 6 and described in more detail below.

In an embodiment, selecting the HCP log menu option displays a listing of dates and times that the record has been accessed by a licensed healthcare professional associated with the patient.

In an embodiment, upgrade button 507 searches the internet or any network for a software upgrade to the currently running program. If a software upgrade is found, the program may automatically install the upgrade.

Average readings section 508 may display information regarding the stored history of blood glucose measurements taken with the blood glucose monitoring device associated with the record. For example, information displayed may include an average blood glucose level, an average number of tests performed each day, or a compliance percentage.

Latest readings table 510 may display a list of blood glucose readings in chronological order taken with the blood glucose monitoring device associated with the record. In an embodiment, the most recent reading is shown at the top. In an embodiment, a side slider bar is used to scroll through the list of readings.

Reading summary 512 may display values of particular interest to the user. For example, reading summary 512 may display the highest and lowest blood glucose readings taken. In another example, reading summary 512 may display percentages relating to how many blood glucose readings have had levels which were low, normal, high, or very high.

Reading history 514 may display average blood glucose readings during a variety of events. Example of events may include before and after meals, before and after exercising, before and after having a snack, etc. Reading history 514 may display averages taken over a customizable time period. In an embodiment, reading history 514 may display averages taken over 7 days, 30 days, or 90 days. In an embodiment, reading history 514 displays blood glucose readings for a specific day.

Average reading graph 516 displays average blood glucose readings taken over a customizable time period in any graphical format. Examples of graphical formats include, but are not limited to, line graphs, scatterplots, bar graphs, etc.

Received messages section 518 may display a list of the most recent messages received by the blood glucose monitoring device associated with the record. The messages may include any type of message including default messages, personalized messages, triggered messages, or messages alerting the patient to order more test strips. In an embodiment, the time that the message was received is also included with each message displayed.

Print report section 520 allows the user to create a printout of the record. The record may be transferred into any suitable file format to be printed including, but not limited to, ADOBE PDF file, .txt file, .doc file, etc. The printed record may be chosen to include glucose reading data over a certain time period. For example, the printed record may include glucose reading data over the past 7 days, past 30 days, or past 90 days.

FIG. 6 displays an embodiment of patient clinical profile screen 600 which may include patient name 602 and date 604 as previously described. Patient clinical profile screen 600 may also include a normal range input 606, a max high value input 608, a time period 610, and a graphical slider bar 612. As illustrated in FIG. 6, patient clinical profile screen 600 may include a plurality of the noted elements for different time periods. The various elements associated with each time period may each be changed by the user separately between the different time periods. Patient clinical profile screen 600 may also include an update button 614.

The patient clinical profile allows the user to select which blood glucose reading ranges should be considered to be low, normal, high, or very high at various time periods throughout the day. This level of customization is important since nominal blood sugar levels may vary from user to user depending on numerous factors such as genetics, daily habits, etc. Examples of time periods include before or after a meal, before or after exercising, and at night before going to sleep.

Normal range input 606 may include two text fields allowing the user to input the range of blood glucose levels that should be considered "normal" for the given time period. Max high value input 608 may include a single text field allowing the user to input the maximum blood glucose level that is considered to be in the "high" range. Once all inputs have been entered, during the associated time period, any blood glucose measurement below the inputted normal range will register as a "low" reading, any measurement between the normal range will register as a "normal" reading, any measurement higher than the normal range but lower than the max high value will register as a "high" reading, and any measurement higher than the max high value will register as a "very high" reading.

Graphical slider bar 612 may be shown to graphically display the various glucose range settings for each time period 610, wherein each range is separated by widgets 613*a-c*. In an embodiment, graphical slider bar 612 may be used to input the glucose ranges for each time period by sliding widgets 613*a-c* along graphical slider bar 612.

Update button 614 is used to submit the changes made to the clinical profile. The program returns to patient data summary screen 500 after the user selects update button 614.

Figure 7:
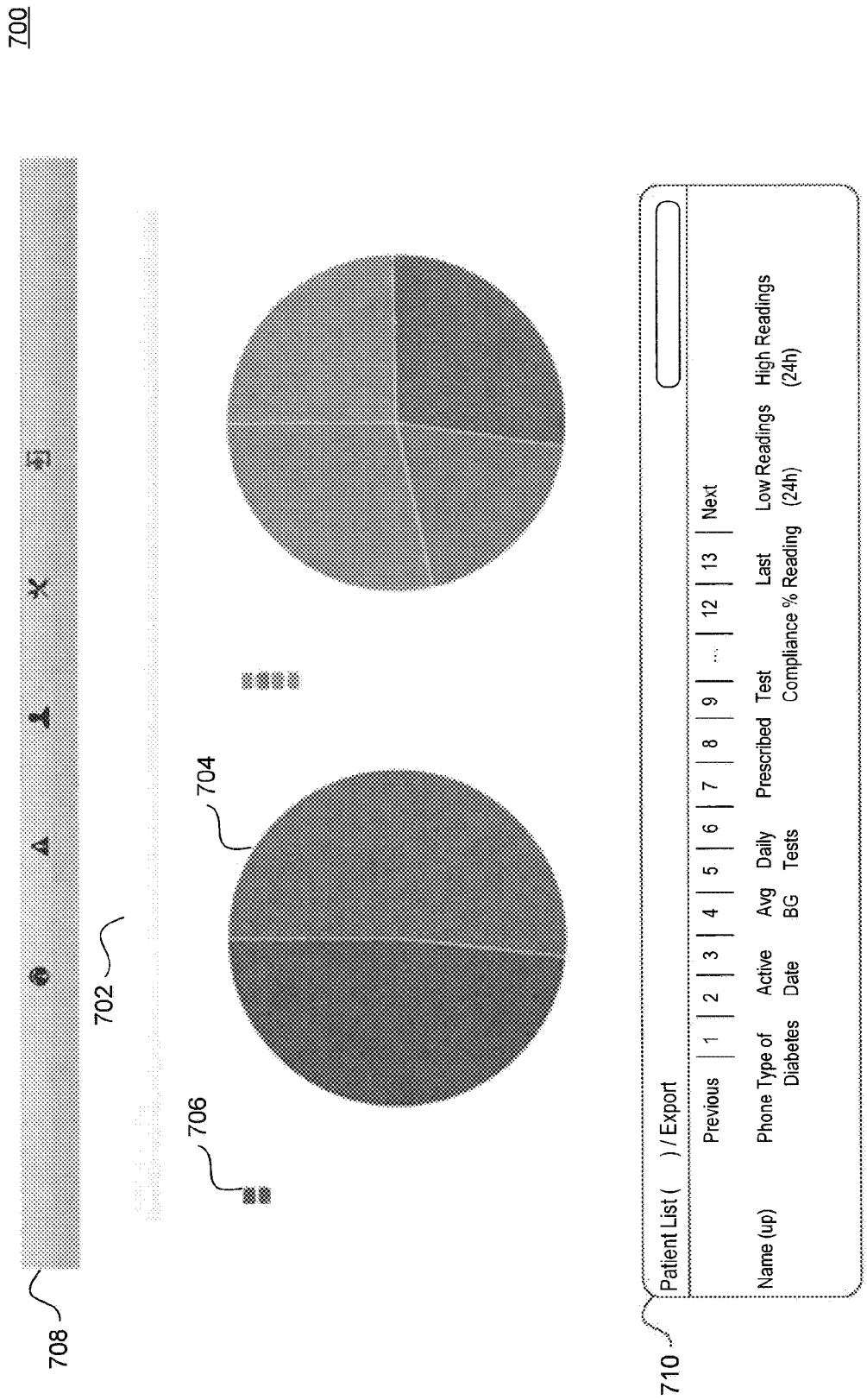
FIG. 7 illustrates a screenshot of a data summary on a plurality of patients, according to an embodiment.

FIG. 7 displays an embodiment of a caregiver data summary screen 700 which includes a graphical summary section 702, a caregiver menu bar 708, and a patient list 710. Graphical summary section 702 may further include one or more of a patient summary graph 704 along with a corresponding graph legend 706.

Caregiver data summary screen 700 is provided to assist caregivers in monitoring a plurality of their patients, each with an associated blood glucose monitoring device. At the top of caregiver data summary screen 700, caregiver menu bar 708 may be provided to display icons which allow the user to either navigate to other pages or to access drop down menus. For example, one icon may produce a dropdown menu containing menu options for the data to be displayed in graphical summary section 702. In another example, one icon may navigate the user to a page listing all of the patients that have received a referral by the logged-in caregiver. In another example, one icon may navigate the user to an administration page, which allows the user to change their basic profile information, set which default messages should be sent out to all patients, and access a script editor as will be discussed in more detail below. Another icon, when selected, may allow the user to log out of the software program. In an embodiment, caregiver menu bar 708 may continue to exist at the top of the page regardless of the content shown on the rest of the page.

Graphical summary section 702 may contain one or more graphs displaying data relating to all of the patients under supervision of the logged-in caregiver. Examples of graphs include, but are not limited to, pie graphs, line graphs, bar graphs, scatterplots, etc. Examples of patient data to display include age, type of diabetes, gender, state of residence, average blood glucose level, and compliance. In the illustrated example of FIG. 7, patient summary graph 704 is a pie chart with corresponding graph legend 706.

Patient list 710 includes a listing of each patient associated with the logged-in caregiver. Patient list 710 may provide various information about each patient including, but not limited to, phone number, type of diabetes, activation date, average blood glucose level, prescribed number of daily tests, compliance percentage, most recent blood glucose reading, etc.

Figure 8:
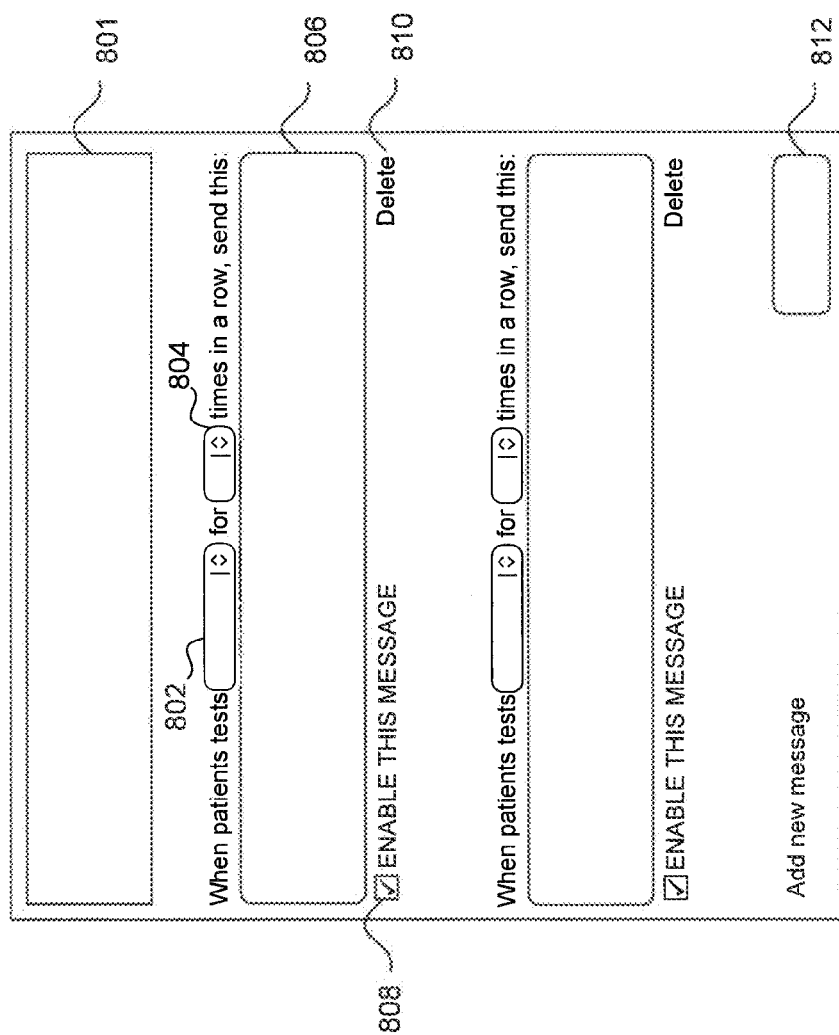
FIG. 8 illustrates a screenshot of a script editor, according to an embodiment.

FIG. 8 illustrates an embodiment of a script editor 800. Script editor 800 may be accessed via an administration page as previously described. In an embodiment, script editor 800 includes a personal message field 801, reading threshold 802, an iteration threshold 804, a message field 806, an enable checkbox 808, a delete button 810, and a save button 812. It should be noted that script editor 800 may be used to create one or more different scripts to be executed.

Script editor 800 allows the user to make changes to scripts executed by a rules engine on networked computer 112. The scripts are executed in response to received blood glucose readings from a blood glucose monitoring device and may return a triggered message if certain criteria is met. The criteria as well as the content of the triggered message may be changed using script editor 800. Regardless of whether the criteria is met or not, the executed scripts will return any enabled default messages or personalized messages to the blood glucose monitoring device in response to a received blood glucose reading.

Reading threshold 802 may display a dropdown menu when selected. The associated dropdown menu may allow the user to choose between various blood glucose reading identifiers such as, for example, "Low", "Normal", "High", etc. Similarly, iteration threshold 804 may include a dropdown menu when selected to choose a number of consecutive readings that fit the identifier chosen in reading threshold 802. When the criteria comprising reading threshold 802 and iteration threshold 804 are met upon receiving a blood glucose measurement, a triggered message comprising text entered into message field 806 is sent to the blood glucose monitoring device.

In an embodiment, script editor 800 is used to edit the scripts for all patients under supervision of the logged-in caregiver. In another embodiment, script editor 800 is used to edit different scripts for each patient under supervision of the logged-in caregiver.

As an example, a script for a particular patient includes reading threshold 802 set to "Very High", iteration threshold 804 set to "5", and message field 806 containing the text, "You have tested very high 5 straight times. Please call me!" In this example, if the particular patient transmits a "Very High" blood glucose measurement five straight times using a particular blood glucose monitoring device, than the script will produce the triggered message entered into message field 806 and transmit the triggered message to the particular blood glucose monitoring device.

Enable checkbox 808 may be used to either enable or disable the associated script. If disabled, the triggered message will not be sent to the blood glucose monitoring device even if the criteria had been met. The script may be re-enabled at any time. Delete button 810 may be used to delete the associated script.

Script editor 800 also allows a user to enter a personalized message into personal message field 801. A personalized message may be associated with only a particular patient. In one embodiment, the personalized message will be transmitted to the blood glucose monitoring device associated with the patient upon receiving the next blood glucose measurement from the blood glucose monitoring device. In another embodiment, the personalized message is transmitted to the blood glucose monitoring device immediately after selecting a submit button (not shown) displayed within script editor 800.

Save button 812 may be selected by the user to save the changes made in script editor 800. Selecting save button 812 returns the user to caregiver data summary screen 700.

Figure 9:
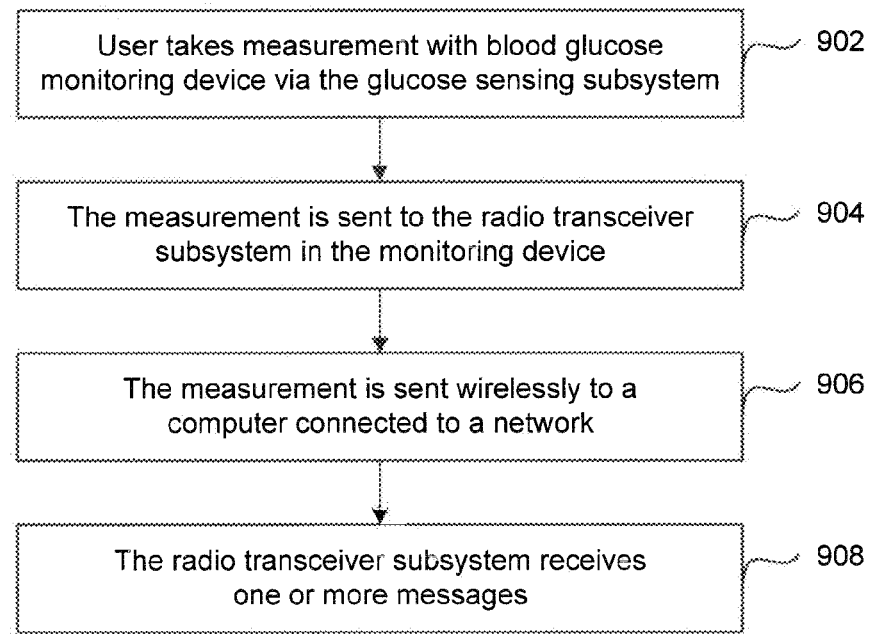
FIG. 9 is a diagram illustrating a method performed by a blood glucose monitoring device, according to an embodiment

FIG. 9 illustrates an exemplary measurement method 900 performed by blood glucose monitoring device 104 after taking a blood glucose measurement. It should be understood that measurement method 900 can be one of many methods performed by device 104 either in parallel or sequentially.

At block 902, a measurement is performed via the glucose sensing subsystem within the blood glucose monitoring device according to an embodiment. The glucose sensing subsystem applies a reference voltage to the blood sample and measures a current response produced from an electrochemical reaction on the test strip. The measured current is compared to a calibration curve and is translated into a voltage, the magnitude of which corresponds to the glucose level in the sample.

At block 904, the voltage calculated at block 902 is sent to the radio transceiver subsystem within the blood glucose monitoring device. The radio transceiver subsystem generates a signal which is modulated by the voltage.

At block 906, the signal which has been modulated by the voltage is wirelessly transmitted to a networked computer. The signal may be encrypted by the radio transceiver subsystem prior to transmission. Any encryption technique known to those skilled in the art may be utilized including, but not limited to, two-factor authentication, 128-bit encryption, etc. The signal received by the networked computer may be decrypted by the networked computer, and the data relating to the blood glucose measurement may be stored in a record within a database on the networked computer.

At block 908, one or more messages returned from the networked computer are received by the radio transceiver subsystem in response to the measurement transmission at block 906. The one or more messages may include any of the message types previously described including default messages, triggered messages, personalized messages, or a low-supply message alerting the user to purchase more test strips. The low-supply alert may include an offer to purchase strips. Further, a user/patient may place an order by responding to the low-supply message via device 104. Networked computer may be configured to receive the order and to initiate a business process that will result in fulfillment of the order, including shipping the ordered test strips to the user/patient associated with the particular device 104 from which the order was placed. In addition to ordering test strips, the networked computer may send a message to device 104 that includes an offer to order related supplies for use with the particular device. Still further, the user may be prompted or provided with an offer to order other merchandise related to his/her needs but not necessarily related to any medical condition.

Figure 10:
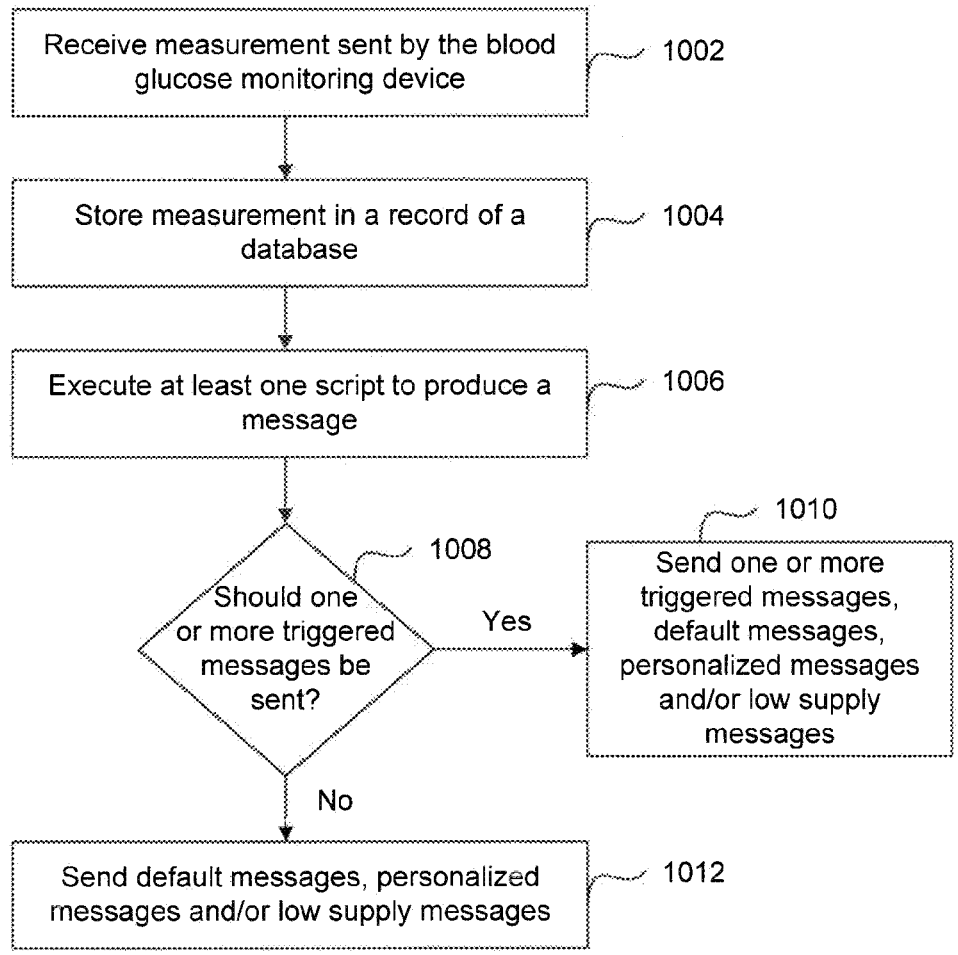
FIG. 10 is a diagram illustrating a method performed by a networked computer, according to an embodiment.

FIG. 10 describes an exemplary server method 1000 performed by a networked computer upon receiving a glucose measurement from a blood glucose monitoring device. It should be understood that server method 1000 can be one of many methods performed by a networked computer either in parallel or sequentially.

At block 1002, a blood glucose measurement sent from the blood glucose monitoring device is received by the networked computer. The received signal is demodulated/decoded to retrieve for analysis the data relating to the measured blood glucose level.

At block 1004, the retrieved blood glucose level is stored in a record of a database. Each record corresponds to a unique blood glucose monitoring device. The records may be accessed by a remote computer and graphically displayed through a software program executed by a processor on either the networked computer or the remote computer.

At block 1006, at least one script is executed to produce one or more messages to be returned to the blood glucose monitoring device. In an example, a script may be executed to compare past measurements and determine whether a triggered message should be sent. In another example, a script may be executed to produce a personalized message. In another example, a script may be executed to track the number of test strips remaining associated with the blood glucose monitoring device. If the number of test strips is below a certain threshold, a low supply message is produced alerting the patient associated with the blood glucose monitoring device that they are running low on supplies. As discussed above, the networked computer may transmit an offer to order more test strips (or other merchandise), if the number of test strips is below a certain threshold. It should be understood that after all scripts have been executed, a message may not necessarily be produced and returned to the transmitting device 104.

At block 1008, the networked computer determines whether the criteria have been met to send a triggered message.

At block 1010, the criteria associated with one or more triggered messages has been met. The one or more triggered messages along with any default messages, personalized messages, or low supply messages are transmitted to the blood glucose monitoring device.

At block 1012, the criteria associated with any triggered message has not been met. Any default messages, personalized messages, or low supply messages are transmitted to the blood glucose monitoring device.

Figure 11:
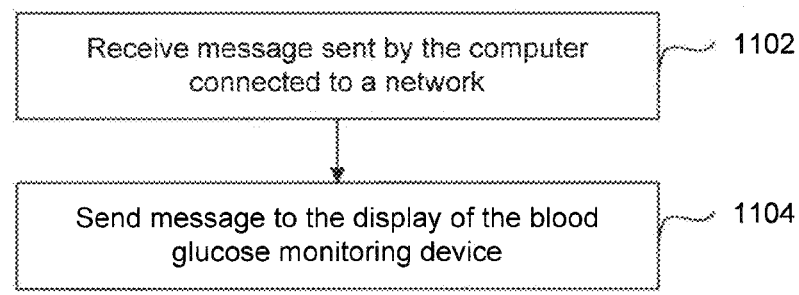
FIG. 11 is a diagram illustrating a method performed by a blood glucose monitoring device, according to an embodiment.

FIG. 11 describes an exemplary received message method 1100 performed by blood glucose monitoring device 104. It should be understood that received message method 1100 can be one of many methods performed by the blood glucose monitoring device either in parallel or sequentially.

At block 1102, one or more messages are received by the radio transceiver subsystem within blood glucose monitoring device 104.

At block 1104, the one or more messages are sent to the display of blood glucose monitoring device 104. The messages may be displayed in any suitable format, such as one at a time, allowing the user to scroll through them, or concatenated together into one message, etc.

In an alternate embodiment, the monitoring system of the invention can be used to monitor other analytes. For, example, the blood glucose sensor may be replaced with a sensor to monitor interstitial fluid glucose, blood coagulation factors, cardiac enzymes, catecholamines, and other biomarkers. Such alternate sensors may operate, for example, using electrochemical or colorimetric sensing techniques as would be apparent to a person skilled in the relevant art.

In this alternate embodiment, the analyte monitoring system comprising a handheld analyte monitoring device and a networked computer. Similar to the blood glucose monitoring device, the analyte monitoring device includes an analyte sensing subsystem configured to measure an analyte from a patient, and a radio transceiver subsystem configured to receive analyte measurements from the analyte sensing subsystem and to transmit the analyte measurements over a wireless communications link. Similar to the blood glucose monitoring system, the networked computer is configured to receive the transmitted analyte measurements. A rules engine running on the networked computer is configured to execute at least one script in response to a received analyte measurement and to produce a message to be sent back to the handheld analyte monitoring device.

In this alternate embodiment, the networked computer includes a database containing records corresponding to each one of a plurality of handheld analyte monitoring devices. Each database record identifies a plurality of messages personalized to a user associated with a particular handheld analyte monitoring device. Message sent back to the handheld analyte monitoring device is selected from the plurality of messages using the script executed by the rules engine.

In yet another alternate embodiment, the monitoring system of the invention can be used to monitor other medical information including, for example, physiologic parameters such as heart rate, blood oxygen saturation, blood pressure, respiration rate, blood pressure, electrocardiographic (ECG) information including ECG morphology using a sensor in communication with an implantable cardioverter defibrillator, body temperature, and the like. Sensors for such physiologic parameters are known in the art and are commercially available.

Figure 12:
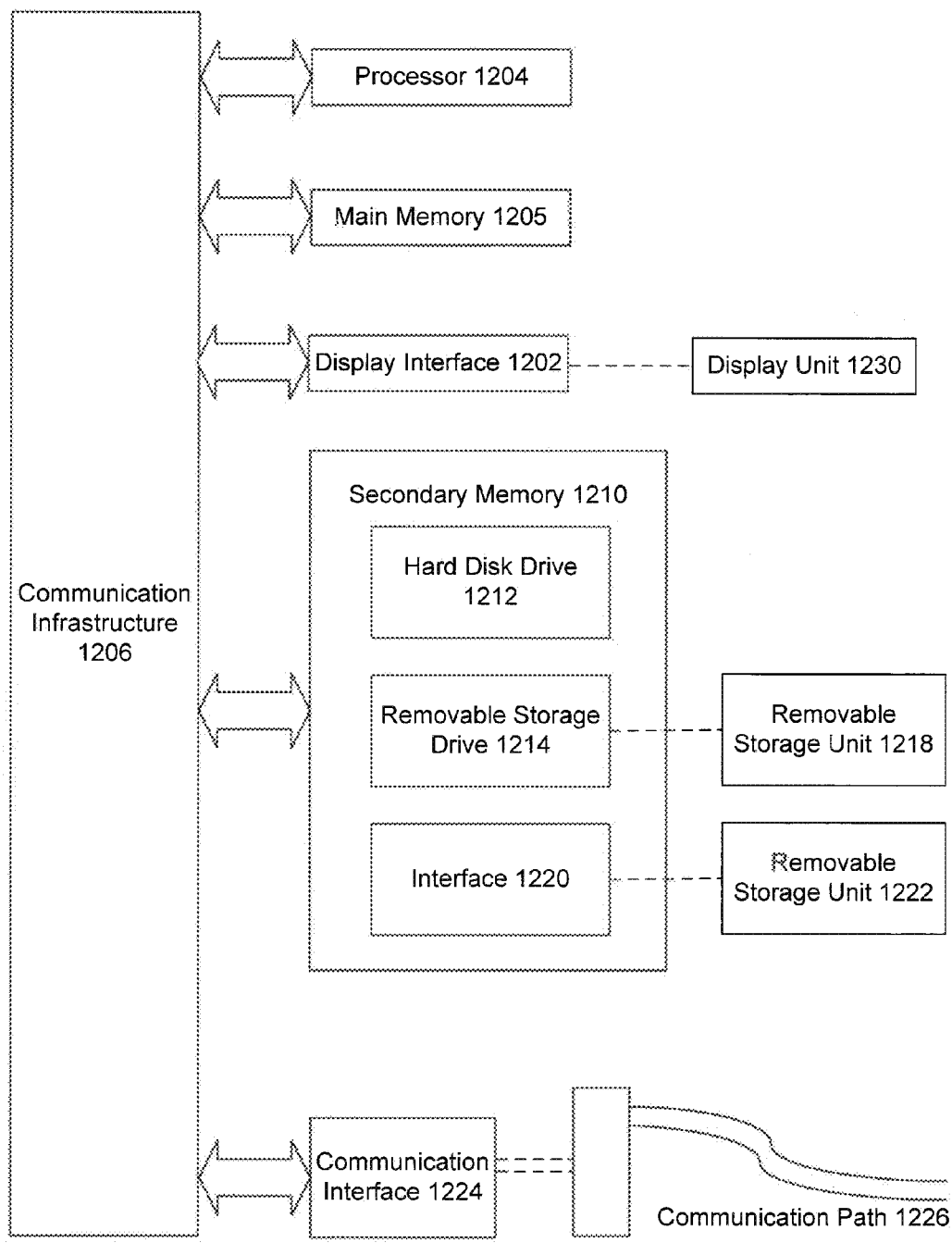
FIG. 12 is an example computer system in which the embodiments, or portions thereof, can be implemented as computer-readable code.

Various aspects of the present invention can be implemented by software, firmware, hardware, or a combination thereof. FIG. 12 illustrates an example computer system 1200 in which the embodiments, or portions thereof, can be implemented as computer-readable code. For example, networked computer 112 carrying out method 1000 of FIG. 10 can be implemented in system 1200. Various embodiments of the invention are described in terms of this example computer system 1200. As another example, remote computer 114 can be implemented in a computer system such as system 1200.

Computer system 1200 includes one or more processors, such as processor 1204. Processor can be a special purpose or a general purpose processor. Processor 1204 is connected to a communication infrastructure 1206 (for example, a bus or network).

Computer system 1200 also includes a main memory 1208, preferably random access memory (RAM), and may also include a secondary memory 1210. Secondary memory 1210 may include, for example, a hard disk drive and/or a removable storage drive. Removable storage drive 1214 may include a floppy disk drive, a magnetic tape drive, an optical disk drive, a flash memory, or the like. The removable storage drive 1214 reads from and/or writes to removable storage unit 1218 in a well-known manner. Removable storage unit 1218 may include a floppy disk, magnetic tape, optical disk, etc. which is read by and written to by removable storage drive 1214. As will be appreciated by persons skilled in the relevant art(s), removable storage unit 1218 includes a computer usable storage medium having stored therein computer software and/or data.

In alternative implementations, secondary memory 1210 may include other means for allowing computer programs or other instructions to be loaded into computer system 1200. Such means may include, for example, a removable storage unit 1222 and an interface 1220. Examples of such means may include a program cartridge and cartridge interface (such as that found in video game devices), a removable memory chip (such as an EPROM, or PROM) and associated socket, and other removable storage units 1222 and interfaces 1220 which allow software and data to be transferred from the removable storage unit 1222 to computer system 1200.

Computer system 1200 also includes a communications interface 1224. Communications interface 1224 allows software and data to be transferred between computer system 1200 and external devices. Communications interface 1224 may include a modem, a network interface (such as an Ethernet card), a communications port, a PCMCIA slot and card, or the like. Software and data transferred via communications interface 1224 are in the form of signals which may be electronic, electromagnetic, optical, or other signals capable of being received by communications interface 1224. These signals are provided to communications interface 1224 via a communications path 1226. Communications path 1226 carries signals and may be implemented using wire or cable, fiber optics, a phone line, a cellular phone link, an RF link or other communications channels. For example, communications path 1226 may correspond to communications link 110 and/or communications link 116. In this example, links 110 and 116 may be networks connected to the global Internet, and communications interface 1224 may be a network card configured to receive TCP/IP-based communications from such networks.

In this document, the term "computer readable storage medium" is used to generally refer to media such as removable storage unit 1218, removable storage unit 1222, and a hard disk installed in hard disk drive 1212. Computer readable storage medium can also refer to one or more memories, such as main memory 1208 and secondary memory 1210, which can be memory semiconductors (e.g. DRAMs, etc.). These computer program products are means for providing software to computer system 1200.

Computer programs (also called computer control logic) are stored in main memory 1208 and/or secondary memory 1210. Computer programs may also be received via communications interface 1224. Such computer programs, when executed, enable computer system 1200 to implement the embodiments as discussed herein. In particular, the computer programs, when executed, enable processor 1204 to implement the processes of embodiments of the present invention, such as the steps in the methods discussed above. Accordingly, such computer programs represent controllers of the computer system 1200. Where embodiments are implemented using software, the software may be stored in a computer program product and loaded into computer system 1200 using removable storage drive 1214, interface 1220, or hard drive 1212.

Embodiments may be directed to computer products comprising software stored on any computer usable medium. Such software, when executed in one or more data processing device, causes a data processing device(s) to operate as described herein.

Embodiments may be implemented in hardware, software, firmware, or a combination thereof. Embodiments may be implemented via a set of programs running in parallel on multiple machines.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed s:

1. A handheld analyte monitoring device comprising:
   an analyte sensing subsystem configured to measure an analyte from a patient;
   a radio transceiver subsystem configured to receive analyte measurements from the analyte sensing subsystem and to transmit the analyte measurements over a wireless communications link, wherein the radio transceiver subsystem is further configured to reduce RF interference with the analyte measurement by deactivating emissions from the radio transceiver subsystem during analyte measurement; and
   a thermally segregated temperature sensor associated with the device, wherein the thermally segregated temperature sensor is disposed at a distal end of a stalk extending outward from an enclosure around the analyte monitoring device.

2. The device of claim 1, wherein the handheld analyte monitoring device further comprises a display to display the analyte level from the analyte sensing subsystem.

3. The device of claim 1, further comprising a shielding structure to isolate at least a portion of the analyte sensing subsystem from the radio transceiver subsystem.

4. The device of claim 1, wherein the radio transceiver subsystem is further configured to control the amount of heat produced by one or more components within the device.

5. A handheld blood glucose monitoring device comprising:
   a glucose sensing subsystem configured to measure a blood glucose level in a blood sample;
   a thermally segregated temperature sensor associated with the glucose sensing subsystem to provide a temperature measurement for use in the blood glucose measurements,
   wherein the thermally segregated temperature sensor is disposed at a distal end of a stalk extending outward from an enclosure around the handheld blood glucose monitoring device; and
   a radio transceiver subsystem configured to receive the blood glucose measurements from the glucose sensing subsystem, and to transmit the blood glucose measurements over a wireless communications link, wherein the radio transceiver subsystem is further configured to reduce RF interference with the blood glucose measurement by deactivating emissions from the radio transceiver subsystem during the blood glucose measurement.

6. The device of claim 5, further comprising a shielding structure configured to isolate at least a portion of the glucose sensing subsystem from the radio transceiver subsystem.

7. The device of claim 5, wherein the the glucose sensing subsystem is electrically isolated from the radio transceiver subsystem.

8. The device of claim 5, wherein the radio transceiver subsystem is further configured to control the amount of heat produced by one or more components within the handheld blood glucose monitoring device.

\* \* \* \* \*